United States Patent
Yokoyama et al.

(10) Patent No.: US 7,329,237 B2
(45) Date of Patent: Feb. 12, 2008

(54) INFUSION THERAPY

(75) Inventors: Shinichiro Yokoyama, Tokyo (JP); Satoshi Saito, Tokyo (JP); Noboru Fukuda, Tokyo (JP); Daisuke Kawabe, Tokyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 11/076,712

(22) Filed: Mar. 10, 2005

(65) Prior Publication Data
US 2005/0159703 A1    Jul. 21, 2005

(51) Int. Cl.
*A61M 29/00*    (2006.01)
(52) U.S. Cl. .................................... 604/101.01
(58) Field of Classification Search ........... 604/101.01, 604/101.02, 101.03, 101.05, 96.01; 606/191–194, 606/915, 916, 917, 919
See application file for complete search history.

(56) References Cited

U.S. PATENT DOCUMENTS 5,135,484 A * 8/1992 Wright .................... 604/28
5,152,277 A * 10/1992 Honda et al. ............ 600/116
6,083,198 A * 7/2000 Afzal ..................... 604/101.01
6,117,105 A * 9/2000 Bresnaham et al. ..... 604/96.01
6,139,517 A * 10/2000 Macoviak et al. ............ 604/8

FOREIGN PATENT DOCUMENTS

| JP | 04-261.668 A | 9/1992 |
| JP | 2000-279.524 | 10/2000 |
| JP | 2001-000448 | 1/2001 |
| WO | WO/01/66028 | 9/2001 |

* cited by examiner

*Primary Examiner*—Manuel Mendez
(74) *Attorney, Agent, or Firm*—Young Basile (57) ABSTRACT

To provide infusion therapy that can effectively transluminally deliver drugs or the like to a target spot without invading areas other than a diseased area. The infusion therapy is for administering a drug, cells or the like, or inserting a treatment instrument into the target diseased area. A blood vessel area including a bifurcated blood vessel connecting to the diseased area is occluded at the distal and the proximal region thereof to form an occluded area, and the drugs or the like are pumped and supplied to the occluded area, which causes the drugs or the like to flow retrogressively and retentively in the bifurcated blood vessel connecting in the occluded area, and be infused and administered to the diseased area.

9 Claims, 8 Drawing Sheets

INFUSION THERAPY

TECHNICAL FIELD

The present invention relates to infusion therapy that can transluminally administer drugs, cells or the like to a diseased area for treatment of cardiac muscle or the like.

BACKGROUND ART

Various types of balloon catheters have been developed in quest of less invasive treatment methods for various kinds of diseases. Such a balloon catheter as a transluminal treatment device is intended to occlude main blood flow temporarily or semipermanently to examine or improve abnormality that occurs. For example, a conventional balloon catheter used in percutaneous transluminal coronary angioplasty is described in Japanese Patent Laid-Open No. 5-285222, in which an expanded balloon is mainly used to dilate a narrowed blood vessel.

For infusion of drugs, cells, or a treatment instrument such as an injection needle into cardiac muscle in which myocardial infarction occurs or may occur, infusion therapy has been considered such that the drugs or the like are directly administered by thoracotomy, or a catheter percutaneously approaches a heart chamber through inferior vena cava, a tip of the catheter is brought close to the cardiac muscle, and the injection needle is inserted into the cardiac muscle via the catheter to administer the drugs or master cells.

The conventional catheter used in this infusion therapy is not intended to occlude a blood vessel, and is thus of a type that uses no balloon. The catheter is usually guided to a target position by a guide wire.

However, the method for directly administering drugs or the like into the cardiac muscle tissue by thoracotomy for the infusion therapy into the cardiac muscle requires opening the chest under general anesthesia and temporarily stopping the heart using extracorporeal circulation, which is highly invasive to the patient.

The infusion therapy in which the catheter percutaneously approaches the heart chamber, and the needle is inserted into the cardiac muscle via the catheter to administer the drugs requires securing a stiff and thick guiding catheter to the inside of the beating heart, which may damage chordae tendineae in the heart chamber to cause postoperative sequelae.

Thus, the infusion therapy into the cardiac muscle tissue using the conventional techniques is incomplete, and essential and more effective treatment means has been desired for myocardial infarction by recovering blood flow in an ischemia area. However, there has been no means for improving an ischemia area that causes myocardial infarction, as well as directly and locally supplying necessary drugs or the like to a diseased area around a body cavity requiring in vivo treatment.

In view of the above described points, the invention has an object to provide a novel infusion therapy.

DISCLOSURE OF THE INVENTION

The inventors have eagerly studied means and a method for effectively transluminally delivering drugs to a target spot without invading areas other than a diseased area using means such as a guiding catheter or the like, and found that a balloon catheter, which has a small diameter so as to be inserted into a guiding catheter and delivered to an in vivo target area, and can create an occluded area in a limited local area without occluding main blood flow, and reversely infuse a drug, cells, a treatment instrument or the like necessary for treatment into the local area only, is suitable for achieving the object of the novel treatment method, thus reaching the invention.

In order to achieve the above described object, the invention provides infusion therapy that preserves at least main blood flow, creates an occluded area occluded from a main blood vessel between two balloons, and supplies drugs, cells, a treatment instrument, or the like according to a treatment method to the occluded area.

Specifically, the invention provides infusion therapy for administering a drug, cells or the like, or inserting a treatment instrument into the target diseased area, characterized in that a blood vessel area including a bifurcated blood vessel connecting to the diseased area is occluded at the distal and the proximal region thereof to form an occluded area, and the drug, cells, treatment instrument or the like are pumped and supplied to the occluded area, which causes the drug, cells, treatment instrument or the like to flow retrogressively and retentively in the bifurcated blood vessel connecting in the occluded area, and be infused and administered to the diseased area.

Next, the invention is characterized in that the infusion therapy uses a balloon catheter for insertion into a blood vessel in which a plurality of lumens extending along an axis are formed in one catheter body, and two expandable balloons expand toward outside with respect to the catheter body are arranged axially in parallel, wherein the plurality of lumens include: an infusion lumen that has an infusion hole communicating with an outside of the catheter body between the two balloons, and can supply drugs, cells, a treatment instrument, or the like to the outside of the catheter body through the infusion hole; balloon lumens that communicate with insides of the two balloons to control expansion of the balloons; a bypass lumen that communicates with the outside of the catheter body in each position distal and proximal, which is outside of the two balloons with respect to a tip of the catheter body, and bypasses an occluded area formed by the two balloons to allow blood flow; and a guide lumen into which a guide wire that guides the catheter body to a target position is inserted, the catheter is inserted into a blood vessel, the two balloons are placed with both end sides of the blood vessel area in between including the bifurcated blood vessel connecting to the diseased area, and expanded to form the occluded area, and the drug, cells, treatment instrument or the like are pumped and supplied to the occluded area through the infusion lumen.

Next, the invention is characterized in that the diseased area is also cardiac muscle tissue, and the blood vessel is a coronary vein.

A device for infusion therapy is preferably used including: a balloon catheter; a guide wire to be inserted into a guide lumen of the balloon catheter; pulsation detection means for detecting pulsation of the heart; and stroke means for causing the guide wire to stroke in synchronization with the pulsation of the heart based on a detection signal of the pulsation detection means, wherein the balloon catheter is a balloon catheter for insertion into a blood vessel in which a plurality of lumens extending along an axis are formed in one catheter body, and two expandable balloons expand toward outside with respect to the catheter body are arranged axially in parallel, characterized in that the plurality of lumens includes: an infusion lumen that has an infusion hole communicating with an outside of the catheter body between the two balloons, and can supply drugs, cells, a treatment instrument, or the like to the outside of the catheter body through the infusion hole; balloon lumens that communicate with insides of the two balloons to control expansion of the balloons; a bypass lumen that communicates with the outside of the catheter body in each position distal and proximal, which is outside of the two balloons with respect to a tip of the catheter body, and bypasses an occluded area formed by the two balloons to allow blood flow; and a guide lumen into which a guide wire that guides the catheter body to a target position is inserted, and the guide lumen communicates with the outside of the catheter body in each position distal and proximal, which is outside of the two balloons to also serve as the bypass lumen.

The two balloons are expanded to form an independent occluded area in the blood vessel between the two balloons to allow the drug, cells, treatment instrument or the like to be supplied through the infusion hole to the local area of the occluded area only. Thus, if a bifurcated blood vessel connects to the occluded area, the drug, cells, treatment instrument or the like are infused into the bifurcated blood vessel to allow the drug, cells, treatment instrument or the like to be supplied to a diseased area through the bifurcated blood vessel.

It is also possible to cause a negative pressure in the infusion lumen to suck and remove, from the infusion hole, substances in the occluded area such as the drugs supplied through the infusion hole.

Blood flow is ensured by the bypass lumen even if the blood vessel is occluded by the balloons, and thus blood flow in the blood vessel can be ensured even if the blood vessel is occluded by the balloons for a predetermined time for conservative therapy or the like.

There is no need for the independent bypass lumen, thus reducing the number of lumens in the catheter body to increase the sectional area of the hole of the bypass lumen.

Pumping action in the bypass lumen by causing the guide wire to stroke in synchronization with the pulsation of the heat improves efficiency of blood circulation by the bypass lumen.

If lost cells of cardiac muscle tissue or a blood vessel can be reconstituted by infusing various factors, drugs, cells or the like, the condition of the disease can be essentially improved. The treatment method to which the invention is suitably applied, that is, the idea of the approach to an organ such that various factors, drugs, and cells are infused into an ischemia area in reverse of blood flow through the coronary vein to substantially treat the organ has been unknown.

One balloon lumen may communicate with the insides of the two balloons. Only one lumen is required for expanding the two balloons, thus reducing the number of lumens in the catheter body to increase a sectional area of a hole of the bypass lumen.

In the invention according to the above claim 3, an unknown approach to an organ is allowed such that various factors, drugs, and cells are infused into a diseased area such as an ischemia area in reverse of blood flow through the coronary vein to substantially treat the organ.

Specifically, master cells or drugs can be administered to target cardiac muscle tissue only through the bifurcated blood vessel connecting to the occluded area formed by the two balloons. In this case, there is no need to directly insert the catheter up to the target cardiac muscle tissue.

BEST MODE FOR CARRYING OUT THE INVENTION

Now, an embodiment of the invention will be described with reference to the drawings.

Figure 1:
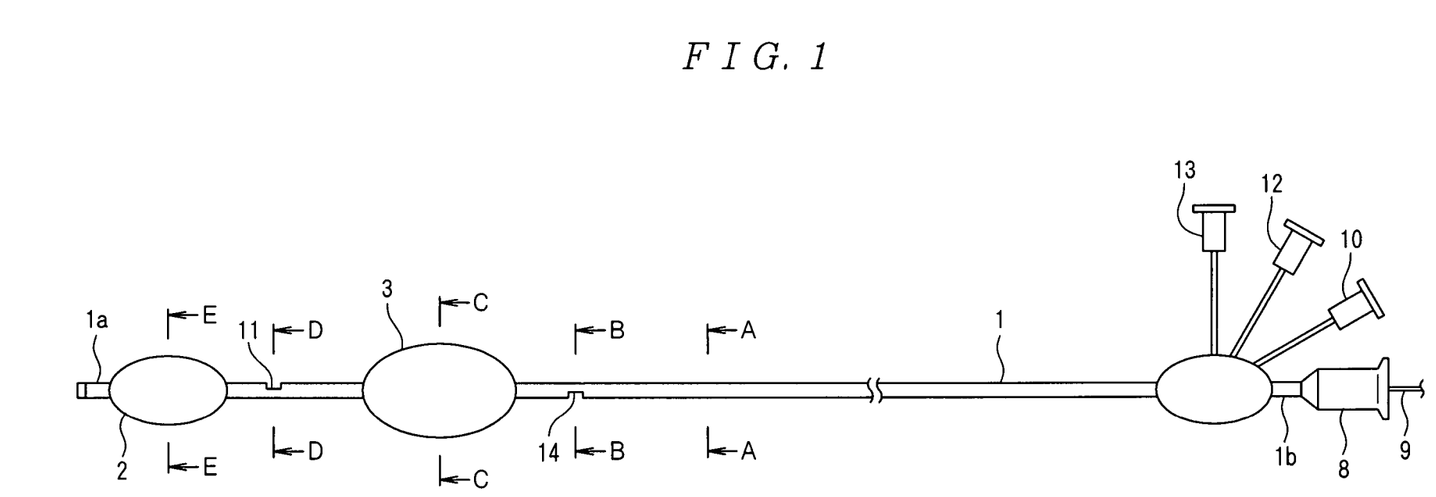
FIG. 1 is a side schematic view of a catheter according to an embodiment of the invention.

FIG. 1 is a side schematic view of a balloon catheter according to an embodiment of the invention, and two balloons 2 and 3 are provided at a predetermined spaced interval on a side of a tip 1*a* of a catheter body 1 constituted by a flexible tube.

Figure 3:
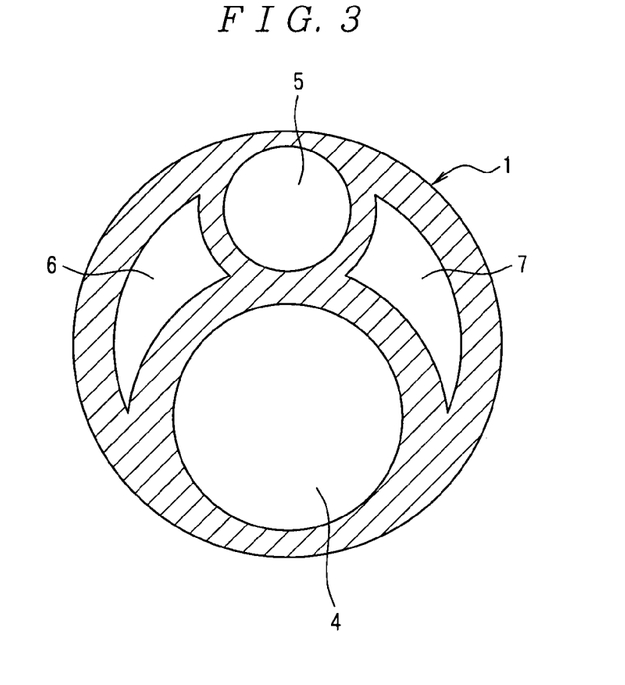
FIG. 3 is a sectional view taken along the line A-A in FIG. 1.

The catheter body 1 includes four lumens as in a sectional view in FIG. 3. The four lumens are a guide lumen 4 that is the largest and also serves as a bypass lumen, an infusion lumen 5, and two pairs of balloon lumens 6 and 7 communicating with the balloons 2 and 3.

The guide lumen 4 is a lumen into which a guide wire 9 is inserted from a guide wire port 8 of a tail end 1*b*, and extends along the catheter body 1 from the tail end 1*b* to the tip 1*a* and opens at the tip 1*a* of the catheter body 1. A hole 4*a* of the tip 1*a* also serves as a hole proximal to the bypass lumen. Distal and proximal positions are presented herein with reference to the tip 1*a* of the catheter body 1.

Figure 2:
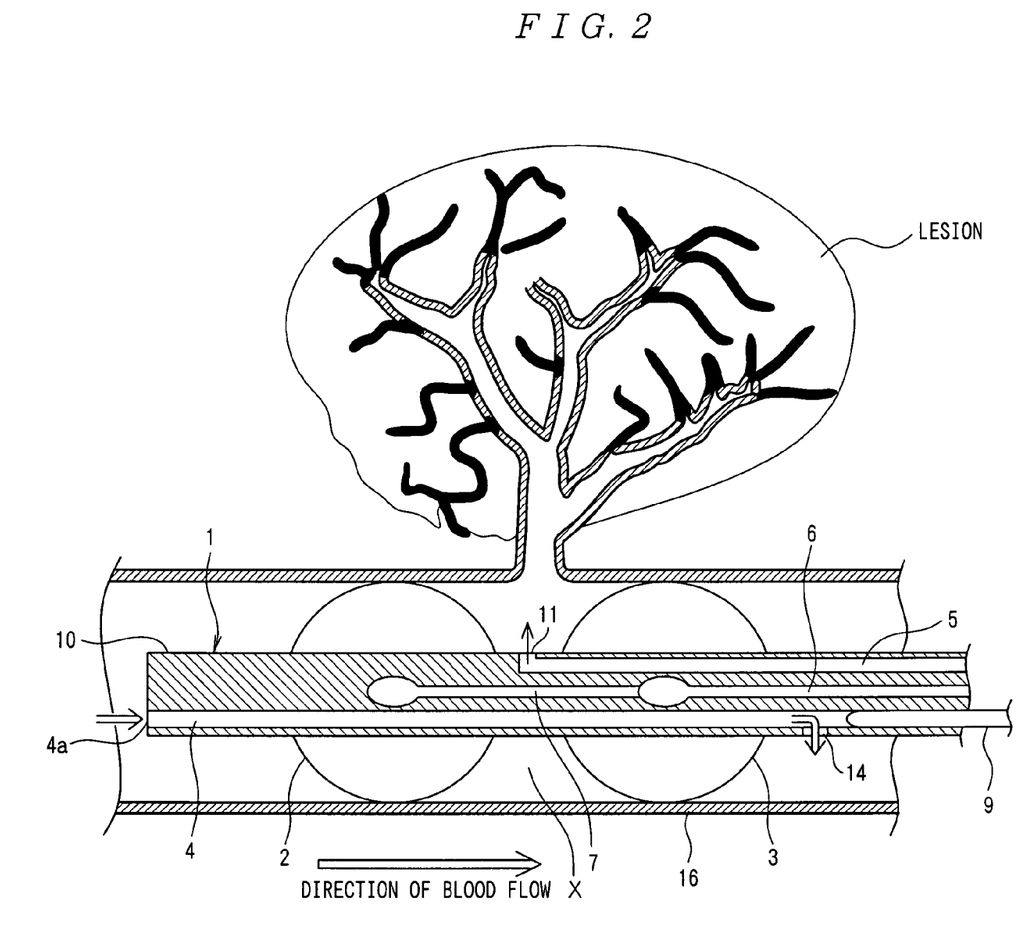
FIG. 2 is a sectional diagram of the catheter in use according to the embodiment of the invention.
Figure 4:
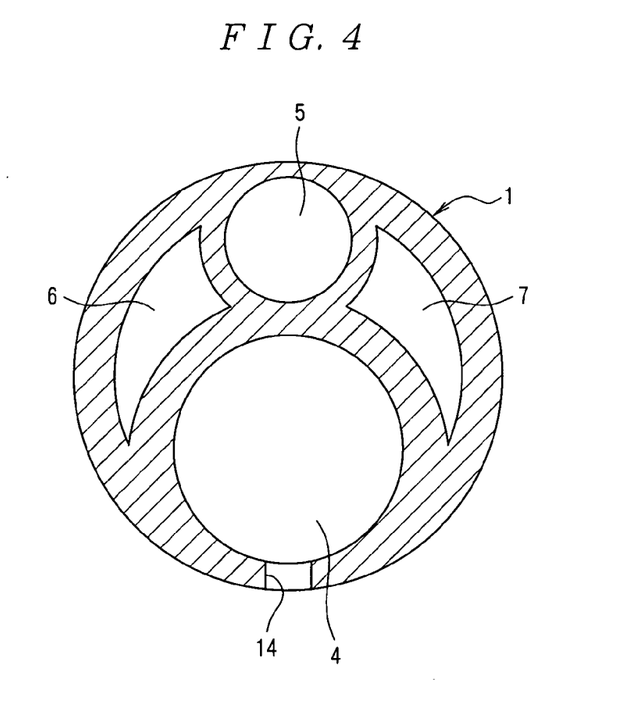
FIG. 4 is a sectional view taken along the line B-B in FIG. 1.

The guide lumen 4 has one or more bypass hole 14 in a position closer to the tail end 1*b* than the two balloons 2 and 3, that is, in a distal position as shown in FIGS. 2 and 4. This allows blood flow in the blood vessel even if the blood vessel is locally occluded by the two balloons 2 and 3.

Figure 5:
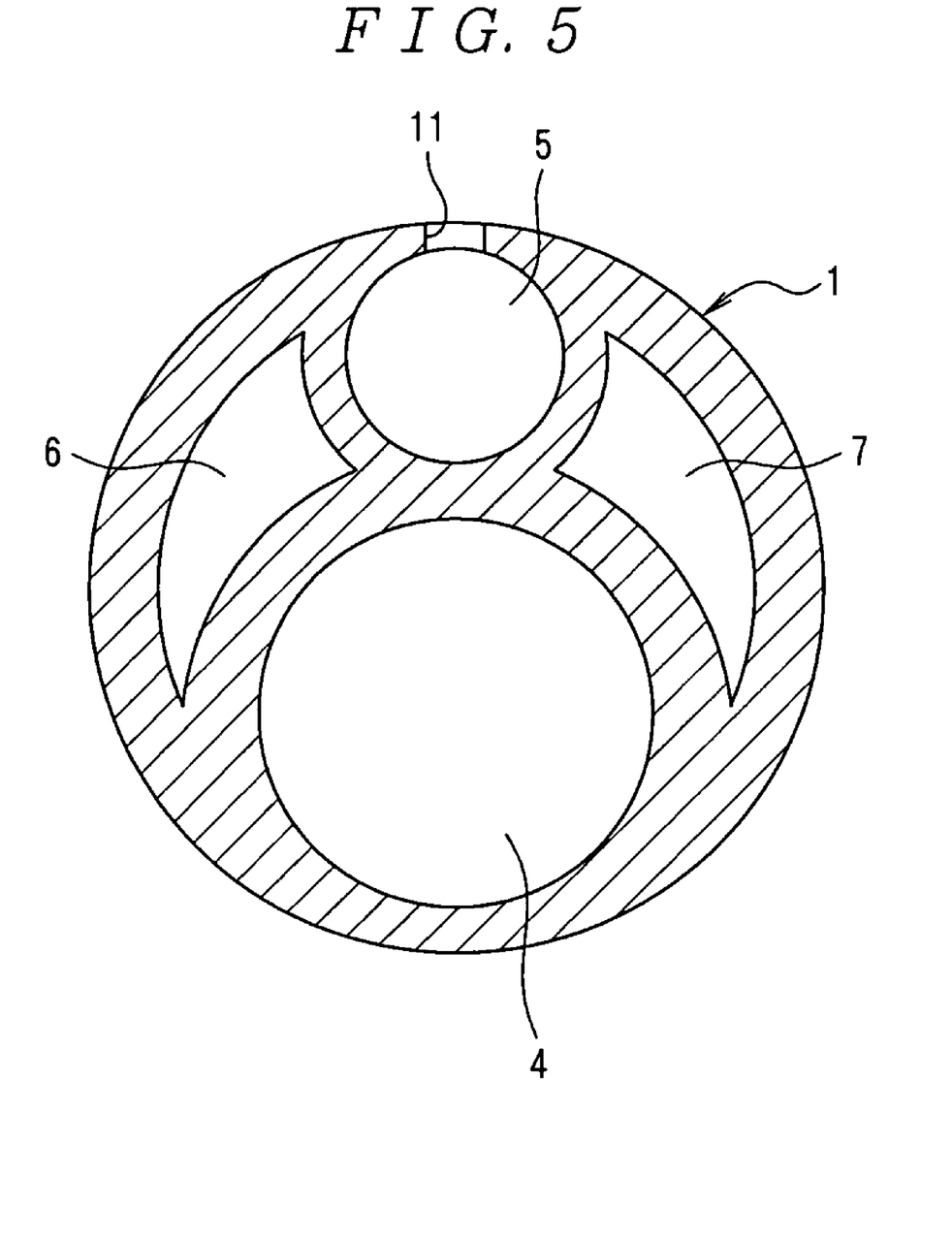
FIG. 5 is a sectional view taken along the line D-D in FIG. 1.

The infusion lumen 5 communicates with an infusion port 10 on the side of the tail end 1*b*, extends from the side of the tail end 1*b* to a position between the two balloons 2 and 3, and communicates with an infusion hole 11 for communication with the outside of the catheter body 1 in the position between the two balloons 2 and 3 as shown in FIGS. 2 and 5.

For the catheter according to the embodiment, a sectional area of the catheter body 1 in terms of a circle preferably has a diameter of 0.5 mmφ to 2 mmφ. The point is that the catheter may be inserted into a vein with play, and a hole sectional area more than a predetermined size may be ensured as the bypass lumen. In the embodiment, the diameter is 0.635 mmφ. A hole sectional area of the guide lumen 4, that is, the bypass lumen in terms of a circle preferably has a diameter of 0.4 mmφ to 1 mmφ. Too small a diameter may cause difficulty in ensuring blood flow of a predetermined amount or more.

Figure 6:
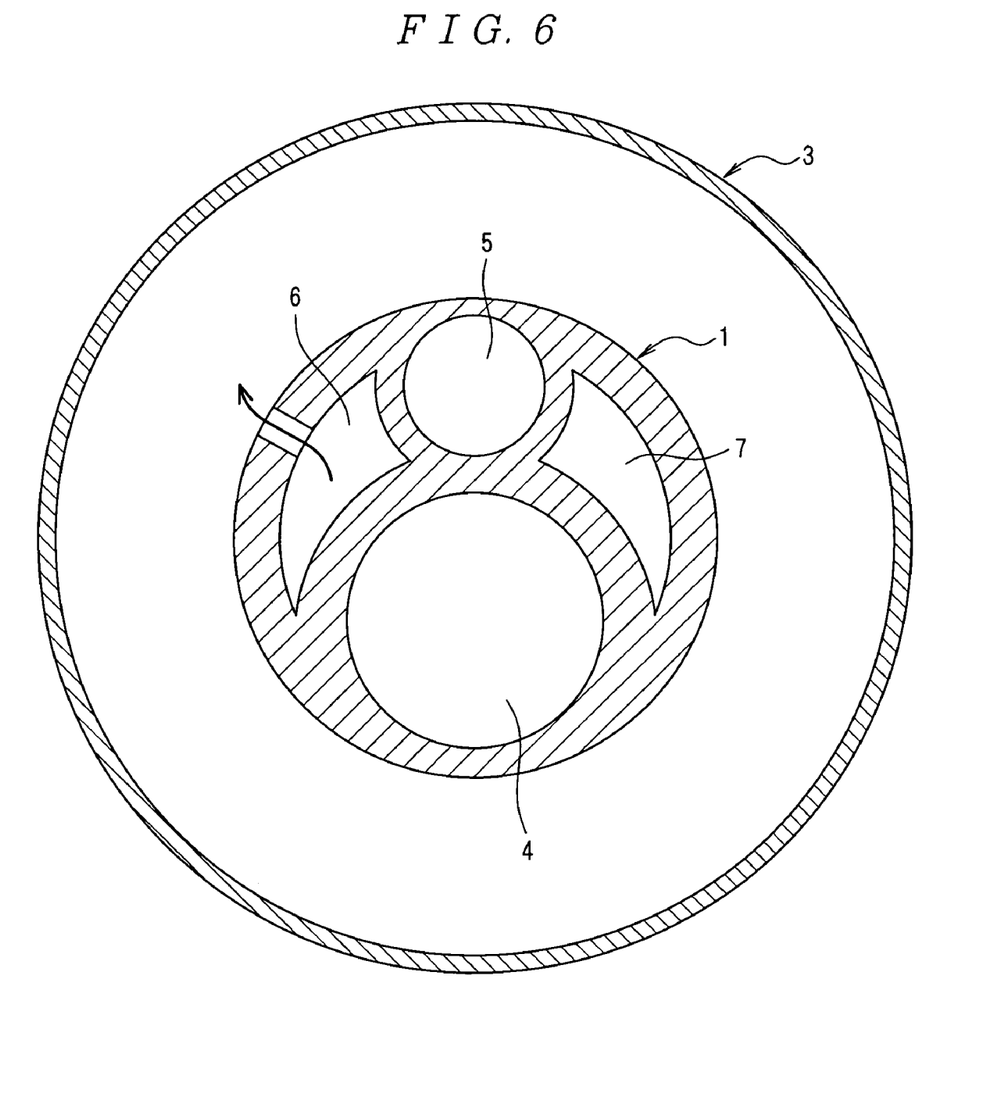
FIG. 6 is a sectional view taken along the line C-C in FIG. 1.
Figure 7:
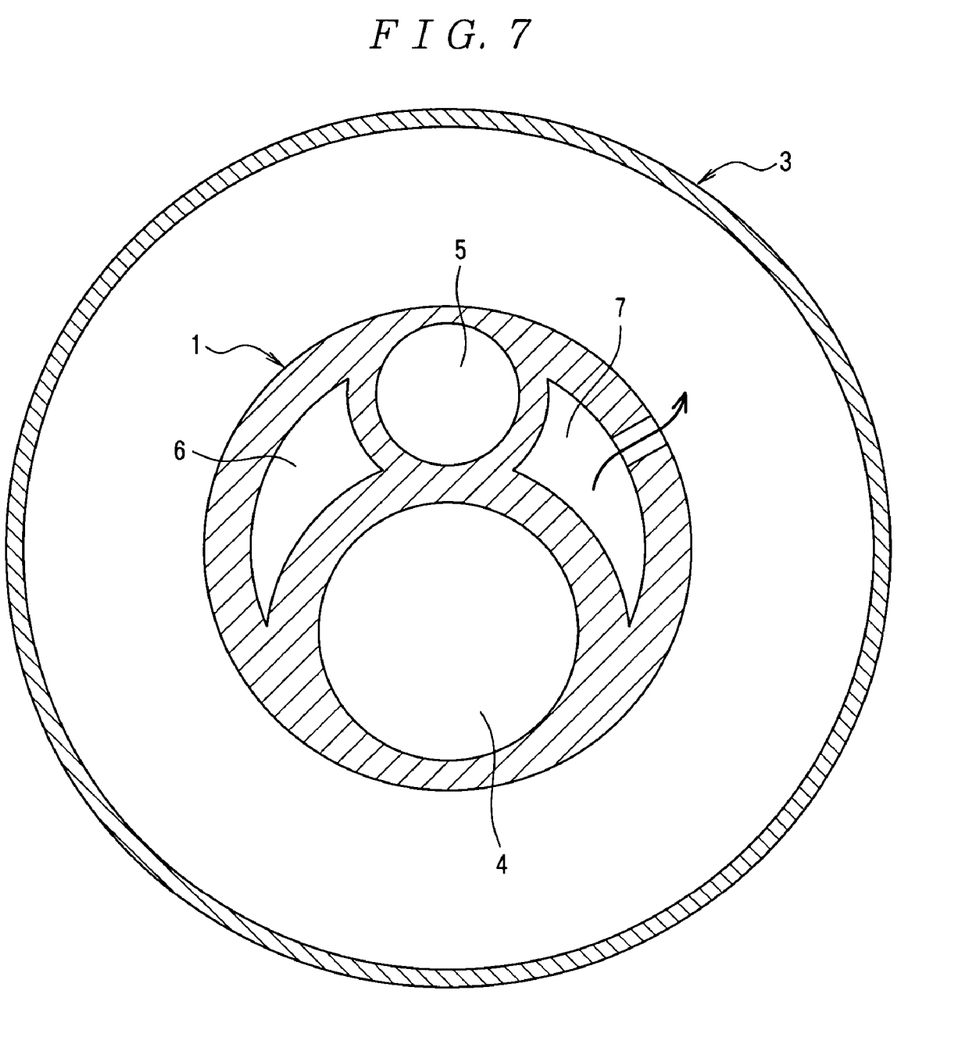
FIG. 7 is a sectional view taken along the line E-E in FIG. 1.

Further, the balloon lumen 6 communicates with a proximal balloon port 12, and the balloon lumen 7 with a distal balloon port 13, respectively, in the tail end 1*b* and extend up to the positions of the balloons 2 and of the corresponding balloons 2 and 3 as shown in FIGS. 2, 6 and 7.

In FIG. 1, the two balloons 2 and 3 are shown having different sizes, but may have the same size, or the distal balloon 3 may be larger. The point is that the balloons may occlude the blood vessel without damaging the blood vessel when expanding.

Further, the guide wire 9 is provided that is inserted into the guide lumen 4 from the guide wire port 8.

Next, an example of use or the like of the balloon catheter having the above described configuration will be described.

Use in treatment of a lesion (an ischemia area), that is, use when drugs, cells or the like are infused into cardiac muscle of a diseased area will be now described by way of example.

Figure 8:
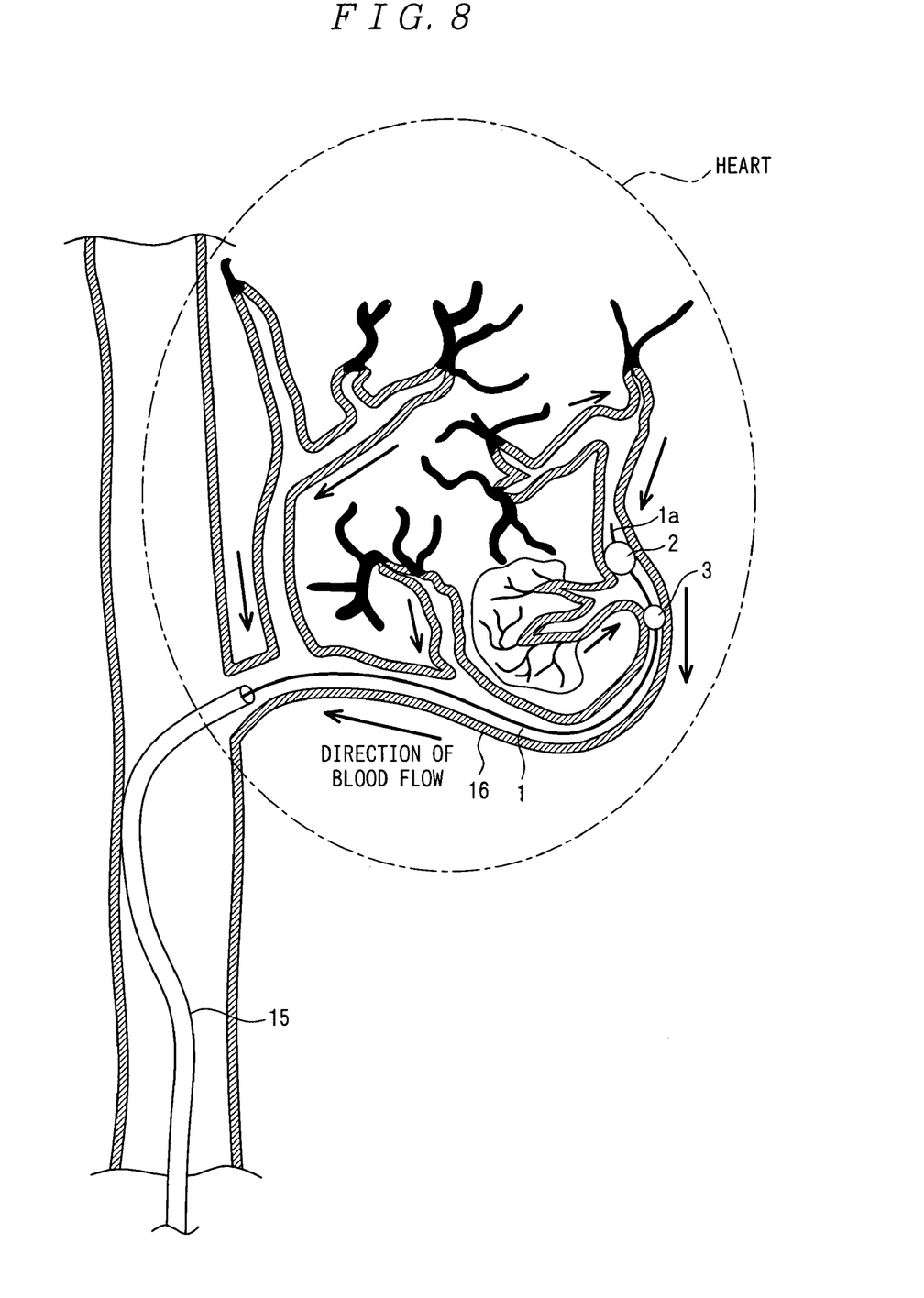
FIG. 8 illustrates use of the catheter according to the embodiment of the invention.

As shown in FIG. 8, a guiding catheter 15 is inserted up to an outlet of a coronary vein 16 and held therein.

Then, the balloon catheter according to the invention previously combined with the guide wire 9 is inserted through the guiding catheter 15 into the coronary vein 16 in reverse of the blood flow to adjust so that a blood vessel area surrounding the lesion (an area including a bifurcated blood vessel connecting to the lesion) is placed between the two balloons 2 and 3 as shown in FIG. 2.

Next, the guide wire 9 is pulled back until the tip of the guide wire 9 is brought to a position near and distal to a bypass hole (the state in FIG. 2). This causes the hole of the tip 4a of the guide lumen 4 to communicate with the bypass hole to allow blood flow bypassing the outside of the catheter body 1 at the positions of the two balloons 2 and 3.

Around the time of the operation of the guide wire 9, gas is pumped to the balloon lumens 6 and 7 to expand the balloons 2 and 3 and locally occlude the blood vessel, thus forming an occluded area X between the balloons 2 and 3.

Next, drugs to be administered to the lesion are pumped from an infusion port. The pumped drugs pass through the infusion lumen 5, and are supplied into the occluded area X with a predetermined pressure from the infusion hole 11. Further, the increase in the pressure in the occluded area X causes fluid in the occluded area X to reversely flow in the bifurcated blood vessel connecting in the occluded area X, and be then infused and administered to the lesion.

Before the administration of the drug, cells or the like, or insertion of the treatment instrument, a negative pressure may be caused in the infusion lumen 5 to suck and remove all or part of the blood in the occluded area X and then supply the drug, cells, treatment instrument or the like.

As described above, by using the catheter according to the embodiment, even if the main blood vessel that forms the local occluded area X including a treatment area or a bifurcated blood vessel connecting to the treatment area is occluded by the balloons 2 and 3, the drug, cells, treatment instrument or the like can be supplied to the local treatment area only while ensuring forward and reverse blood flow in the main blood vessel bypassing the occluded area X. Specifically, a substance required for treatment can be infused into a limited occluded area only while ensuring the blood flow.

The balloons 2 and 3 do not dilate a narrowed area, but preferably minimize leaks of drugs from the occluded area X.

The drawings show only one bifurcated blood vessel in the occluded area X, but the occluded area X is usually set so as to include one to ten bifurcated blood vessels.

An injection needle may be exposed from the infusion hole 11 and directly inserted into the diseased area to infuse drugs, or suck and remove fluid or cells in the diseased area by the inserted injection needle.

In the embodiment, the balloon lumens 6 and 7 are formed for each of the balloons 2 and 3, but one balloon lumen 6 and one balloon lumen 7 may be connected to the two balloons 2 and 3 to reduce the number of lumens in the catheter body 1.

In the embodiment, the guide lumen 4 also serves as the bypass lumen, but the invention is not limited to this. An independent bypass lumen may be provided.

Figure 9:
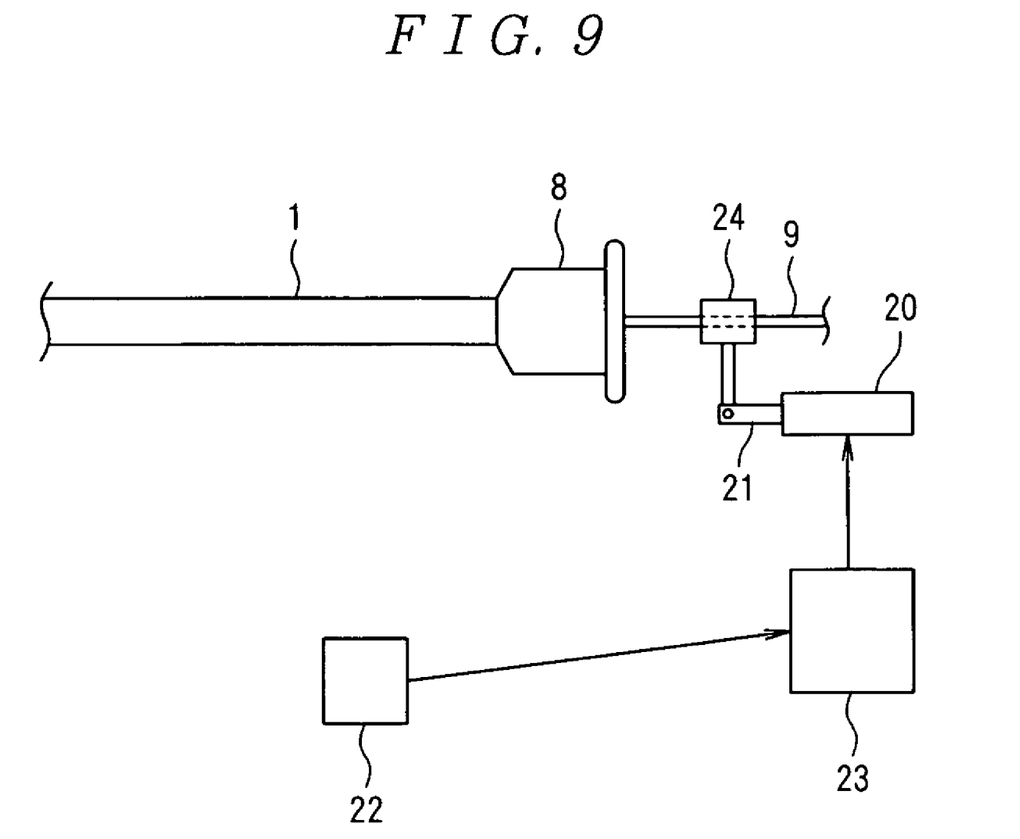
FIG. 9 is a schematic block diagram of an operation of a guide wire according to the embodiment of the invention.

The guide wire 9 pulled back to the position distal to the bypass hole may be adapted to stoke by a predetermined amount of stroke in synchronization with pulsation of the heart. For example, as shown in FIG. 9, a cylinder rod 21 of a piston 20 is connected to the guide wire 9. A signal from known pulsation detection means 22 for detecting heart beat is adapted to be supplied to a controller 23, and the controller 23 instructs the piston 20 to reciprocate in synchronization with the signal from the pulsation detection means 22. Reference numeral 24 denotes a grip that connects to the rod of the piston 20 to grip the guide wire 9.

In this way, causing the guide wire 9 to stroke in synchronization with the pulsation allows efficient blood flow via the bypass lumen by pumping action.

In the above description, the case where the piston 20 constitutes the body of the stroke means is illustrated, but a stepping motor or the like may constitute the stroke means.

INDUSTRIAL APPLICABILITY

As described above, the invention allows a drug, cells, a treatment instrument or the like to be supplied to a local area only while ensuring blood flow.

The invention claimed is:

1. An infusion therapy for administering a substance required for treatment or inserting a treatment instrument into the target diseased area, the therapy comprising:
   a blood vessel area including a bifurcated blood vessel connecting to said diseased area occluded at a distal and proximal region thereof to form an occluded area, without dilating the blood vessel, and wherein said substance required for treatment is pumped and supplied to the occluded area, which causes said substance to reversely flow in the bifurcated blood vessel connecting in said occluded area, and be infused and administered to said area, and allowing flow in the blood vessel even if the blood vessel is locally occluded by providing one or more bypass hole in a position closer to a tail end.

2. An infusion therapy according to claim 1, characterized in that said infusion therapy uses a balloon catheter for insertion into a blood vessel in which a plurality of lumens extending along an axis are formed in one catheter body, and two expandable balloons expand toward outside with respect to the catheter body are arranged axially in parallel,
   wherein said plurality of lumens comprises:
   an infusion lumen that has an infusion hole communicating with an outside of the catheter body between said two balloons, and can supply a substance required for treatment to the outside of the catheter body through said infusion hole;
   balloon lumens that communicate with insides of said two balloons to control expansion of said balloons;
   a bypass lumen that communicates with the outside of the catheter body in each position distal and proximal, which is outside of said two balloons with respect to a tip of the catheter body, and bypasses an occluded area formed by the two balloons to allow blood flow; and
   a guide lumen into which a guide wire that guides the catheter body to a target position is inserted,
   and said catheter is inserted into a blood vessel, said two balloons are placed with both ends sides of the blood vessel area including the bifurcated blood vessel connecting to said diseased area, and expanded to form said occluded area, and said substance required for treatment is pumped and supplied to said occluded area through the infusion lumen.

3. An infusion therapy according to claim 1, characterized in that said diseased area is cardiac muscle tissue, and said blood vessel is a coronary vein.

4. An infusion therapy for administering a drugs or cells, or inserting a treatment instrument into the target diseased area, said therapy comprising the steps of:

occluding a blood vessel area including a bifurcated blood vessel connected to said diseased area at a distal and proximal region of the target diseased area for forming an occluded area without dilating the blood vessel;

pumping and supplying said drugs or cells to the occluded area;

subsequently causing the drugs or cells to reversely flow in the bifurcated blood vessel connected in the occluded area for infusing and administering the drugs or cells to the diseased and; and, allowing flow in the blood vessel even if the blood vessel is locally occluded by providing one or more bypass hole in a position closer to a tail end.

5. The infusion therapy according to claim 4, further comprising the steps of:

forming in one catheter body of a balloon catheter a plurality of lumens, extending along an axis in the one catheter body, wherein said plurality of lumens include an infusion lumen, balloon lumens, a bypass lumen, and a guide lumen;

expanding two expendable balloons outside with respect to the catheter body and arranging the two balloons axially in parallel;

communicating an infusion hole in the infusion lumen with an outside of the catheter body between said two balloons;

supplying the outside of the catheter body with drugs or cells or a treatment instrument through said infusion hole;

communicating the balloon lumens with insides of the two balloons to control expansion of the two balloons;

communicating the bypass lumen with the outside of the catheter body in each position distal and proximate, which is outside of said two balloons with respect to a tip of the catheter body and bypassing the occluded area formed by the two balloons to allow blood flow via the bypass lumen;

inserting a guide wire into the guide lumen for guiding the catheter body to a target position;

inserting the balloon catheter with the plurality of lumens and the one catheter body into the blood vessel;

placing the two balloons with both end sides of the blood vessel area including the bifurcated blood vessel connected to the diseased area;

expanding the two balloons to form said occluded area; and pumping and supplying said drugs or cells or treatment instrument to the occluded area through the infusion lumen.

6. The infusion therapy of claim 4 wherein the step of occluding a blood vessel includes the step of occluding a coronary vein at a distal and proximal region of a cardiac muscle tissue.

7. An infusion therapy for administering a drug or cells, or inserting a treatment instrument into the target diseased area, said therapy comprising:

means for occluding a blood vessel area including a bifurcated blood vessel connecting to said diseased area at a distal and proximal region of the target diseased area for forming an occluded area without dilating the blood vessel;

means for pumping and supplying the drugs or cells to the occluded area;

means for subsequently causing the drugs or cells to reversely flow in the bifurcated blood vessels connected in the occluded area for infusing and administering the drugs or cells to the diseased area; and means for allowing flow in the blood vessel even if the blood vessel is locally occluded by providing one or more bypass hole in a position closer to a tail end.

8. The infusion therapy of claim 7 further comprising:

means for forming in one catheter body of a balloon catheter a plurality of lumens, extended along an axis in the one catheter body, wherein said plurality of lumens include an infusion lumen, balloon lumens, a bypass lumen, and a guide lumen;

means for expanding two expendable balloons outside with respect to the catheter body and arranging the two balloons axially in parallel;

means for communicating an infusion hole in the infusion lumen with an outside of the catheter body between said two balloons;

means for supplying the outside of the catheter body with drugs or cells or a treatment instrument through said infusion hole;

means for communicating the balloon lumens with insides of the two balloons to control expansion of the two balloons via the balloon lumens;

means for communicating the bypass lumens with the outside of the catheter body in each position distal and proximate, which is outside of said two balloons with respect to a tip of the catheter body and means for bypassing the occluded area formed by the two balloons to allow blood flow via the bypass lumen;

means for inserting a guide wire into the guide lumen for guiding the catheter body to a target position;

means for inserting the balloon catheter with the plurality of lumens and the one catheter body into the blood vessel;

means for placing the two balloons with both end sides of the blood vessel area including the bifurcated blood vessel connected to the diseased area;

means for expanding the two balloons to form said occluded area; and means for pumping and supplying said drugs or cells or treatment instrument to the occluded area through the infusion lumen.

9. An infusion therapy for administering a substance required for treatment or inserting a treatment instrument into a target diseased area, the therapy comprising:

a formed occluded area in a blood vessel area including a bifurcated blood vessel connecting to the disease area, said formed occluded area occluded at a distal and proximal region of the diseased area without dilating the blood vessel, wherein said substance required for treatment is pumped and supplied to the occluded area causing the substance to reversely flow in the bifurcated blood vessel connecting in the occluded area for infusion and administration to the diseased area; and, one or more bypass holes in a position downstream from the formed occluded area in the direction of the blood flow for allowing blood flow in the blood vessel even if the blood vessel is locally occluded.

* * * * *

UNITED STATES PATENT AND TRADEMARK OFFICE
CERTIFICATE OF CORRECTION

PATENT NO. : 7,329,237 B2
APPLICATION NO. : 11/076712
DATED : February 12, 2008
INVENTOR(S) : Shinichiro Yokoyama et al.

It is certified that error appears in the above-identified patent and that said Letters Patent is hereby corrected as shown below:

Column 4, Line 23; Delete "1 a" and insert -- 1a --, therefore.

Column 4, Line 61; After "1b" insert -- , --.

Column 4, Line 62; After "and" insert -- 3 to communicate with inside --.

Column 7, Line 13; In Claim 4, after "diseased", delete "and" and insert -- area --, therefore.

Signed and Sealed this

Seventeenth Day of June, 2008

JON W. DUDAS
*Director of the United States Patent and Trademark Office*